United States Patent
Fladda et al.

(10) Patent No.: US 6,332,951 B1
(45) Date of Patent: *Dec. 25, 2001

(54) METHOD FOR MEASURING THE CONTENT OF BLEACHING CHEMICALS USED FOR BLEACHING CELLULOSE FIBERS

(75) Inventors: Gerdt Fladda, Täby; Stig Norder, Säffle; Bertil Olsson, Nol, all of (SE)

(73) Assignee: BTG Källe Inventing AB, Säffle (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/331,462

(22) PCT Filed: Dec. 23, 1997

(86) PCT No.: PCT/SE97/02210

§ 371 Date: Jun. 21, 1999

§ 102(e) Date: Jun. 21, 1999

(87) PCT Pub. No.: WO98/30884

PCT Pub. Date: Jul. 16, 1998

(30) Foreign Application Priority Data

Dec. 23, 1996 (SE) .................................................. 9604829

(51) Int. Cl.$^7$ ............................... C12Q 1/30; D21C 9/16
(52) U.S. Cl. ................... 162/49; 162/72; 162/78; 435/27; 435/277; 435/278
(58) Field of Search ................................ 435/27.4, 283.1, 435/20, 277, 278; 536/56; 422/50, 68.1; 162/49, 238, 70, 72

(56) References Cited

U.S. PATENT DOCUMENTS

| | | |
|---|---|---|
| 1,874,339 | 8/1932 | Norton . |
| 4,192,708 | * 3/1980 | Bergstrom et al. ..................... 162/49 |
| 4,427,772 | * 1/1984 | Kodera et al. ......................... 435/27 |
| 5,081,045 | 1/1992 | McGill ................................. 436/155 |
| 6,124,111 | * 9/2000 | Fladda et al. .......................... 435/27 |

FOREIGN PATENT DOCUMENTS 0052834   6/1982   (EP) .

* cited by examiner

Primary Examiner—Steve Alvo
(74) Attorney, Agent, or Firm—Ostrolenk, Faber, Gerb & Soffen, LLP

(57) ABSTRACT

A method and a device for measuring the content of chemicals used in connection with bleaching of preferably cellulose fibers in a pulp, suspension for the purpose of providing a better and more uniform product quality and preventing overdosage of the bleaching chemical used. According to the invention a measurement sample is derived from a predetermined volume of the pulp suspension after or during the bleaching. Further, a catalyst in the shape of the enzyme catalase is added to the sample, which is agitated so that the bleaching chemical is decomposed and oxygen gas is generated, which oxygen gas pushes out a certain sample volume for the measurement sample, which sample volume is directly or indirectly converted, e.g. via a simple algorithm, to a value representing the content of the bleaching chemical used.

5 Claims, 2 Drawing Sheets

METHOD FOR MEASURING THE CONTENT OF BLEACHING CHEMICALS USED FOR BLEACHING CELLULOSE FIBERS

BACKGROUND OF THE INVENTION

1. Field of the Invention

The present invention relates to a method and a device for measuring the content of chemicals in connection with bleaching carried out with the use of bleaching agents, preferably cellulose fibres in a pulp suspension. The object is to provide a better and more uniform product quality and to prevent overdosing of the bleaching chemical used.

2. Brief Description of the Related Art

In the pulp and paper industry, the bleaching of cellulose fibres is essential to the final product quality. Principally, the bleaching has two aims, namely first to create a continuation of the lignin-separating process, which consists of cooking in the manufacture of chemical pulps, and second to remove the dark colour given to the pulp by certain organic substances so that a certain brightness is created. Previously, chemicals based on chlorine were extensively used as bleaching agents. However, law changes, partly triggered by massive public opinion concerning influence on the environment, have enforced chlorine-free bleaching processes, in which context e.g., peroxide bleaching has been used to an increasing extent both for chemical and mechanical pulp as well as for recycled fibres. Peroxide is a relatively expensive chemical, for which reason a better control of the bleaching process would mean substantial savings in terms of chemical consumption and, at the same time, provide a better and more uniform product quality. To achieve better control it is necessary to measure the content of peroxide in the pulp after the bleaching, the so-called residual peroxide. A condition for a good bleaching result is that there always exists a certain content of residual peroxide, the amount of which in turn depends on the type of pulp and the type of bleaching process. On the other hand, too high a content of residual peroxide means economical losses since it is caused by an overdosing of the bleaching chemical, or bleaching agent, used in the process.

The content of residual peroxide is measured for the reason that the content of bleaching agent can vary from a few ppm up to several thousand ppm. The content is usually determined in the laboratory by means of a titration method. To carry out the analysis in a laboratory is normally not advisable in connection with automatic process control because the results are not available after a sufficiently short delay and also because the laboratory analysis requires much staff work. Better supervision of, e.g., the residual peroxide content accordingly requires access to an instrument for continuous (on-line) measurements during the process. The necessary measurement frequency may, depending on the bleaching process used, vary between approximately 3 to 10 minutes. The measurement is then carried out on a filtration sample from the bleached pulp suspension, the concentration of which may be 15% and higher. The sample can be derived either by means of a special sampler, extracting a fibre-free sample from the pulp suspension, or directly out of the reject from a press which can be located after the bleaching tower. The properties of the filtrate vary with the bleaching process and with the sampling position. Normally, peroxide bleaching is carried out at a pH value of 8.5–11.5 and at a temperature between 850 and 120° C. (lower temperatures are to be used for recycled pulp). The filtrate can contain, inter alia, chemicals used to stabilize peroxide and complex binding of metal ions and to adjust the pH value. In addition thereto, there can also be found in the filtrate suspended material in the form of fine fibre material, filling agents (clay, chalk . . . ), collodial lignin, printing inks, etc.

The instruments today used in the pulp industry for on-line measurement of the residual peroxide content are generally based on the titration principle or on electrochemical methods. However, those instruments, for various reasons, do not operate satisfactorily. From a result point of view, automatic titration instruments perform rather well but the measurement rate is much too slow, up to 30 minutes between results and, in addition thereto, they require various chemicals, which must be handled with great care and which generate waste products detrimental to the environment. Further, the instruments also require much maintenance, which naturally is a drawback in connection with continuous operation. Instruments based on electrochemical methods, such as polarography or voltametry, have low selectivity when used together with bleaching filtrates derived from pulp from the forest industry, because such filtrates have a complex composition resulting in unsatisfactory accuracy and reproducibility. In addition thereto, those instruments are relatively insensitive at low residual peroxide contents.

SUMMARY OF THE INVENTION

The object of the present invention is to provide a method and a device of the type mentioned above, by means of which method and device the disadvantages above referred to are eliminated. The features characterizing the invention appear from the subsequent patent claims.

The present invention provides a method and a device yielding a quick result which can be available in less than 3 minutes. A further advantage is that the method is selective, with only peroxide showing up in the result. Also, the character of the sample does not disturb the measurement result. The method according to the invention is based on utilizing the instability of the bleaching chemical causing decomposition, oxygen being formed during that process, in combination with use of a catalyst constituted by the enzyme catalase, the content of the bleaching chemical being determined according to a manometric or other method during decomposition of the chemical. When correctly used, catalase has the significant advantage that its activity is independent of the pH value existing in normal bleaching processes and a measurement can take place within a relatively wide temperature range. The method also covers a wide measurement interval, 0–3000 ppm. Throughout all of that range, the measurement can be carried out with high accuracy and reproducibility maintaining the same measurement instrument arrangement and calibration. Further, the chemical used is completely harmless, and the instrument structure can be simple and reliable and its calibration need is minimal.

BRIEF DESCRIPTION OF THE DRAWINGS

An embodiment exemplifying the invention will now be described in greater detail, with reference being made to the accompanying drawings.

DETAILED DESCRIPTION OF PREFERRED EMBODIMENTS

Figure 1:
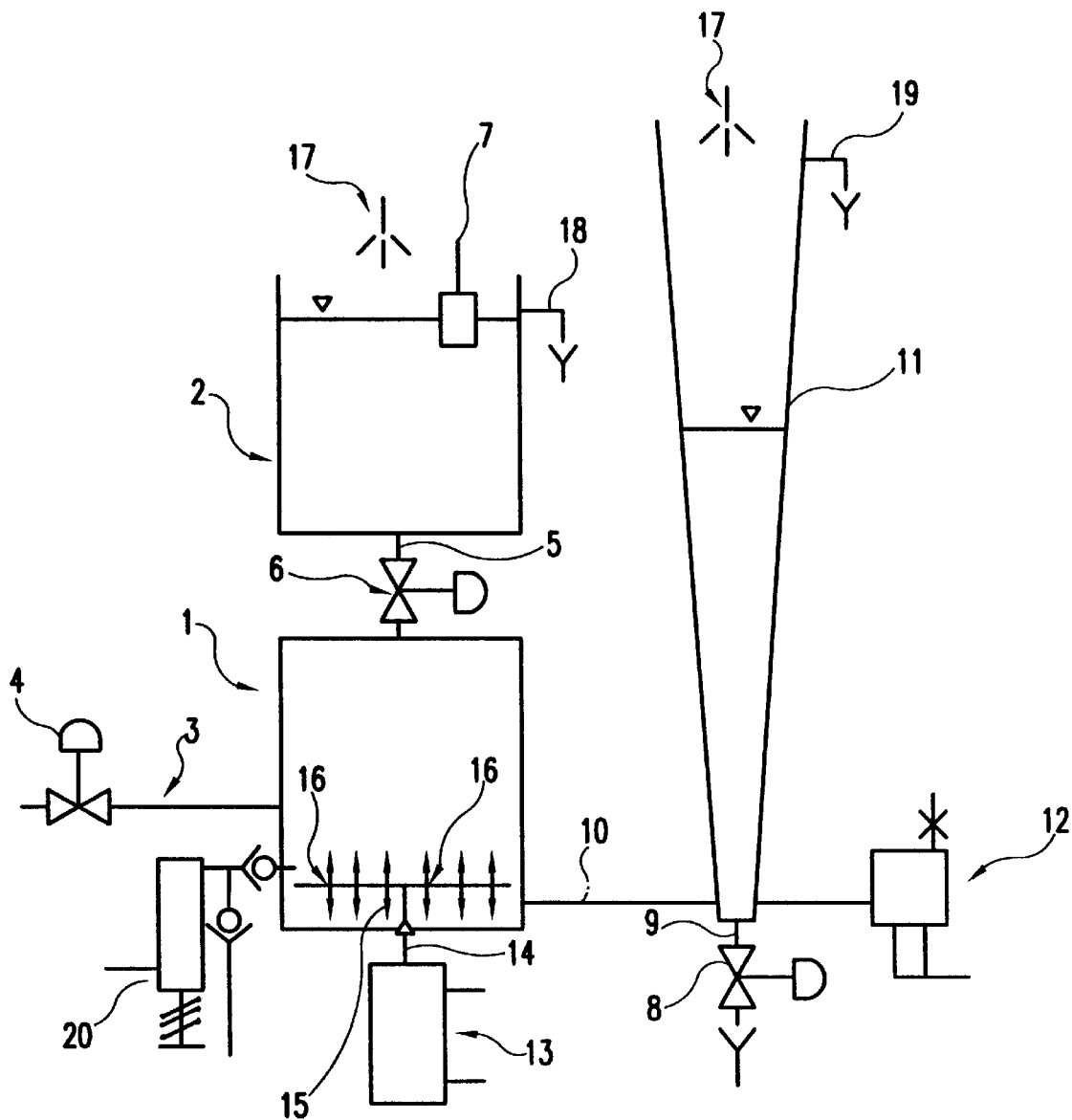
FIG. 1 is a diagrammatic view of a measurement device according to the present invention.

The new measurement method is based on the well-known instability of the bleaching chemical, meaning that, during certain conditions, it easily decomposes, oxygen being generated in the process. Measurement of the oxygen gas content then represents the bleaching chemical content in the sample. Spontaneous decomposition may occur already at reasonably high temperatures and accelerates in the presence of a catalyst, which can be manganese, platinum, etc. The catalyst can either be inside the measurement container in a solid, heterogeneous state or dosed in liquid form for each measurement. The decomposition of the bleaching chemical, e.g., peroxide, then takes place according to $$H_2O_2 \xrightarrow{\text{Catalyst}} H_2O + 1/2 O_2$$

The oxygen gas content can suitably be determined according to a manometric method, e.g., by registration of the pressure build-up, inside a closed measurement container.

The method to determine the peroxide content according to the description above does not constitute a novelty, per se, but it has not before been used for an on-line determination of the residual peroxide content in water from the forest industry or from other industries.

The method according to the invention exhibits especially two essential features, namely: selection of a catalyst and the way in which the oxygen gas measurement is carried out. As to the choice of a catalyst, it is more difficult to realize the principle involving a solid catalyst in the measurement than to use a liquid catalyst dosed at each individual measurement. This is due, inter alia, to the varying activity of the solid catalyst, depending on changing surface properties due to oxidation and contamination. The liquid catalysts discussed in the literature generally have various drawbacks making it difficult to base a commercial on-line instrument on the use of those substances. The disadvantages can be long reaction times or a low sensitivity, a pronounced pH dependency, the formation of deposits in the measurement vessel or dangerous properties of the substances as seen from a handling and environmental point of view. Potassium permanganate, for example, is a substance which yields a very good and quick reaction in terms of the decomposition of the peroxide. However, during the reaction there are formed in the measurement container deposits of manganese oxide, which are very difficult to remove by a simple washing procedure. The manganese oxide functions as an extra catalyst for the decomposition of the peroxide and disturbs the measurement, especially at low residual peroxide contents. Also, such deposits jeopardize the function of the nozzle for dosing the catalyst.

In contrast thereto, the enzyme catalase is, according to the present invention, used as a catalyst. Catalase is a protein chain which is found in, e.g. potatoes, and is completely harmless from a handling and environmental point of view. It is known that catalase decomposes peroxide at a high rate of effectiveness and is used in other connections, e.g., within the textile industry for the process of removing peroxide by decomposing it into water and oxygen gas. Compared with other catalysts, catalase has the great advantage that its activity exists at all pH values appearing in connection with normal bleaching (pH 8.5–11.5) and within a relatively wide temperature range. The sample must be cooled down at temperatures above approximately 70° C. As to the rest, there is usually no substance present which could affect the activity or "poison" the catalase. Also, the catalase has the great advantage that it can be used in exactly the same way for measuring the content of peracetic acid, which will to an increasing extent be used in the future as a standard bleaching chemical within the pulp and paper industry. Bleaching with paracetic acid takes place within the pH interval 3–4.5. This does not cause any problems in connection with the use of catalase but it is essential that the equipment can tolerate the low pH value. The high-activity catalase recently developed also permits the dosage of catalase per sample to be kept at a very low volume, meaning that a relatively low supply volume of catalase in the instrument will suffice for at least two weeks before the staff must make a refilling. From a maintenance point of view, this is most essential.

When the oxygen gas content is to be measured, the sample is normally enclosed in a measurement container, the catalyst is dosed and the overpressure caused by the oxygen gas generation is measured. This calls for a very tight container having, inter alia, expensive special valves. However, due to decomposition of the sample there always exists a risk that the valves will leak due to contamination or jamming fibres. This can naturally cause considerable measurement errors. Another disadvantage accompanying overpressure measurement is that the solubility of the liquid varies in response to the pressure. It is difficult to check this and to compensate for it, and at low contents of residual peroxide, high magnitude errors may occur. For those reasons, overpressure measuring is less accurate in the low content range. For that reason, according to the invention, another method is used to measure the oxygen gas content. Instead of allowing the oxygen gas generated to build up an overpressure inside a closed measurement vessel, the gas volume is caused to push a corresponding amount of the liquid (the sample) into an open vessel communicating with the measurement vessel. The liquid level in the communicating vessel will then be the measure of the peroxide content. The liquid level is measured by means of a pressure sensor installed at the bottom of the level vessel. In addition thereto, the vessel can be given such a shape that the level is, e.g., a logarithmic signal representing the peroxide content. This means that the instrument can operate within a wide measurement range maintaining, as a matter of principle, the same accuracy without the need for any changes in the instrument. This is important, inter alia, in processes involving different pulp qualities having very different residual peroxide contents.

Another advantage of using a communicating measurement vessel is that it will become simpler automatically to diagnose a defect in the measurement signal and to carry out an automatic calibration of the pressure sensor and hence of the peroxide content.

FIG. 1 diagrammatically shows the structure of the measurement system according to a preferred embodiment of the invention. It diagrammatically explains the mode of operation of an instrument which can be used, based on the method according to the invention, for measurement of the content of a bleaching chemical, e.g. residual peroxide. The device for carrying out a measurement according to the invention comprises a measurement container 1 and a container 2, the container 1 serving as a reaction chamber and the container 2 as an overflow vessel. The sample on which the measurement is to be made enters the container 1 through a pipe 3 via a valve 4. The containers 1 and 2 are interconnected by a pipe 5, which likewise is provided with a valve 6 for cutting off the connection between the containers 1 and 2. When a measurement is to be made, the valves 4 and 6 are opened, whereupon the sample in question flows into the containers 1 and 2 up to the activation level for a switch 7 in the container 2 so that the valves 4 and 6 are again closed. During the filling period, a valve 8 is closed, which is connected in an outlet pipe 9 below a level vessel 11, which via a pipe 10 communicates with the container 1. This means that the communicating level vessel 11 will also be filled with sample liquid. When the valve 8 is opened, the vessel 11 is emptied, whereupon the valve 8 is closed. The emptying of the level vessel 11 does not affect the contents of the container 1. This is due to the relatively small, about 6 mm, cross-section of the pipe 10 between the container 1 and the vessel 11. Due to the surface tension of the sample liquid, there cannot in the pipe 10 or in its opening be formed an air bubble that could rise towards the upper portion of the container 1 and push out the sample from the container. Further, the negative pressure in the container 1 prevents out-through of the sample therein. Next, there is added a certain amount of a catalyst chemical, meaning catalase, with the aid of a dosage device 20 connected to the container 1, which causes a corresponding sample volume to be pressed out from the container 1 into the connection pipe 10 between the container 1 and the level vessel 11, which is filled up to a minimum level. This means that a pressure sensor 12 connected to the level vessel will always indicate a certain pressure before the measurement clearly representing the zero point for the measurement and at the same time providing a possibility for a certain function checking (self-diagnostics).

After the dosage, the catalase is mixed with the sample by means of a special agitator 13 located below the container 1 and comprising a rod supporting a disc 15, the diameter of which is slightly less than the inner diameter of the container 1. The disc 15 has a number of through holes 16 and can reciprocate up and down inside the container 1 thus initiating decomposition of the peroxide into water and oxygen gas. The oxygen gas thus formed pushes a corresponding sample volume out from the container 1 and into the level vessel 11 and the changed liquid column level is indicated via the pressure sensor 12. Normally, the reaction is rather rapid initially when most of the peroxide is decomposed. After some time, the reaction is substantially finished, the liquid level in the vessel 11 has a constant position and the pressure signal is with a simple algorithm, converted to a value for the peroxide content expressed in ppm or mg/l. The measurement system is then emptied in the way that the valves 6 and 8 are opened after which the system is cleaned by means of special spray nozzles 17 for clean water, whereupon the next measurement can be started. All of the measuring sequence is controlled by a micro processor system (not shown in the drawing) also handling data collection, result calculation, result presentation and self diagnostics with an alarm function.

The following comments also relate to how to carry out the method with the aid of the disclosed device according to the present invention.

During the measuring process, a sample is pushed out from the container 1 to the vessel 11, which sample still contains some peroxide which has not been decomposed. If the reaction volume is homogenous, the increasing peroxide content will successively reduce the active filtrate volume in a controlled way, which contributes to the logarithmic function without causing increased errors.

When peroxide is decomposed by the addition of catalase, the reaction velocity will be strongly dependent on the stirring of the sample, or rather the amount of mechanical energy transferred to the sample. The reason for this is that due to charging phenomena, the catalase will rather quickly be surrounded by water molecules, thus preventing the catalase from being an active catalyst in the decomposition of peroxide into water and oxygen gas. These catalase-water bindings are strong and can be broken only via a powerful mechanical influence. According to the invention, this is achieved by means of the special agitator 13. Its disc 15 reciprocates rapidly up and down inside the reaction chamber or the first measurement container 1, usually at a frequency of a few dozen movements per minute. The disc 15 is driven by a pneumatic, linear cylinder and its diameter is only a few millimeters less than the inner diameter of the container 1. Accordingly, the stirring action is essential to reach a good measurement result.

The reaction chamber, or the measurement container 1, preferably has a volume of about 400 ml. The height of the container 1 roughly equals its diameter. This has a certain significance as far as the agitation is concerned. The container volume can naturally be varied but it should be borne in mind that the volume should not be that small that the accuracy and the resolution of the measuring method are lost due to the small amounts of oxygen gas generated when the peroxide is decomposed. A greater volume gives a more robust structure, which furthermore is less sensitive to contamination, etc. Another aspect is the amount of dosed catalase, meaning that a greater reaction chamber volume entails a higher catalase consumption. This not only means higher operational costs for the instrument but also that the catalase supply at the instrument must be refilled more often, which is looked upon as a negative factor by the worker staff and by the laboratory staff.

The second measurement container 2 and the level vessel 11 are each provided with an overflow outlet 18, 19, respectively, so that the sample liquid can be diverted to a sewer in case of system failure.

Preferably, the volume of the level vessel 11 should match the volume of the reaction chamber or the measurement container 1 in order to get a maximum resolution within a certain measurement range, e.g., 0–3000 ppm.

The dosage pump for the catalase can consist of commercially available equipment. The dosage amount is not critical in terms of the measurement result as long as a certain catalase overdosage is made. A normal catalase dosage is about 2 ml for a reaction chamber volume of about 400 ml.

When greater temperature variations in the reaction chamber in the container 1 are expected, the equipment should include a temperature sensor correcting gas volume changes. The pressure sensor 12 at the level vessel 11 could be a standard sensor having a good temperature compensation.

Figure 2:
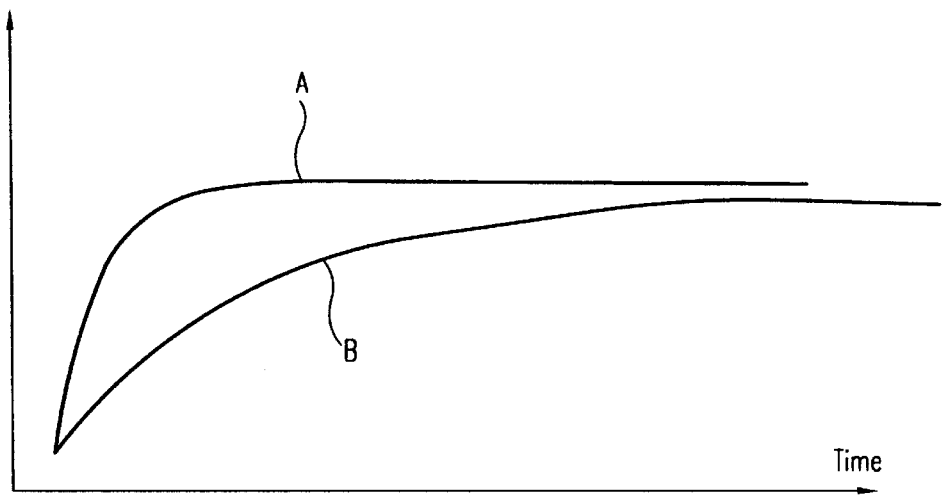
FIG. 2 illustrates the result of the peroxide reaction taking place in the measurement container in FIG. 1 at different agitation conditions, which indicates the measurement signal (liquid level) received during a predetermined time period, and FIG. 3 graphically shows the measurement result for peroxide as a function of the content of peroxide determined in the laboratory by means of titration, the level vessel being arranged to give a logarithmic measurement signal within the measurement interval 0–3000 ppm.

In order to illustrate the results of measurements according to the invention using a device in accordance with FIG. 1, FIG. 2 shows typical results when peroxide is used and for different agitation conditions. It is obvious that an intensive mixing yields a more rapid reaction in terms of the decomposition of the peroxide. In this graphic presentation, the curves A and B relate to vivid and slow agitation, respectively.

Figure 3:
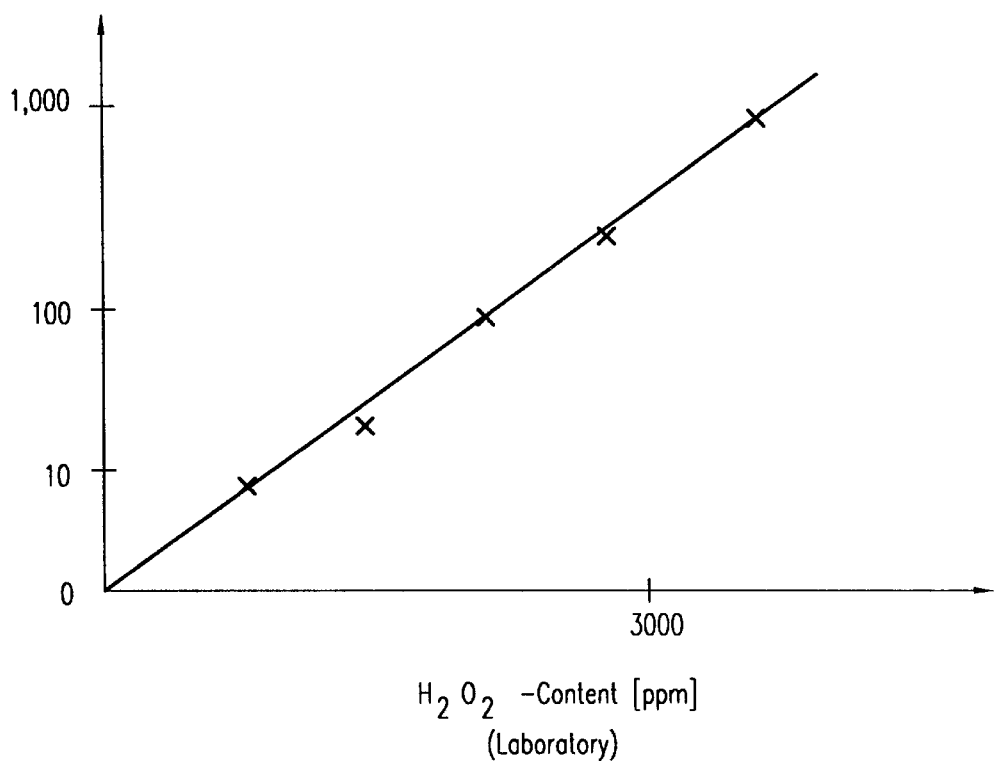

The diagram in FIG. 3 presents the results obtained with the use of peroxide and an instrument according to the invention. The measurement result is here presented as a function of the content of peroxide as determined in the laboratory by titration. In this case, the level vessel was arranged to give a logarithmic measuring signal within the range 0–3000 ppm.

In pulp processes where microbiological activity occurs, generally in a production based on use of recycled fibres, the enzyme catalase is generated by certain microorganisms. Exactly as in the above-described method, the peroxide will then be decomposed into water and oxygen gas so that the amount of peroxide in the fibre suspension is decreased. This is considered a process-technical problem. If the catalase content/catalase activity were indicated, countermeasures would be feasible.

By "inverting" the method described above, it is possible to get information about the amount of catalase in the suspension instead of about the residual peroxide amount. The filtrate from the fibre suspension which can comprise catalase is supplied to the measurement container of the system. However, instead of dosing catalase as is made when the amount of peroxide is to be determined, in this case a predetermined amount of peroxide is dosed. This is followed by the normal measuring sequence including agitation and measurement. If a catalase is present in the sample, the dosed peroxide is decomposed and the amount of gas when generated is a measure of the catalase content/activity. A certain error in the measurement result could occur if the sample would not comprise just catalase but also a certain content of residual peroxide. One can, however, compensate for this, e.g., by alternately measuring the amount of catalase (=peroxide dosage) and the amount of residual peroxide (=catalase dosage).

What is claimed is:

1. A method for measuring the content of chemical substances in connection with their use for bleaching of cellulose fibers, in a pulp suspension, for the purpose of providing uniform product quality and preventing overdosing of a bleaching substance used, comprising:

taking a first sample having a predetermined volume from the pulp suspension after or during the bleaching;

adding a catalase catalyst enzyme to the first sample;

stirring the first sample to cause a decomposition of the bleaching substance and formation of oxygen gas, whereby the oxygen gas thus formed will, from the first sample, push out a second sample volume; and calculating a value representing the content of the bleaching substance used based on the second sample volume.

2. A method as claimed in claim 1, further comprising dosing the first sample with a bleaching chemical.

3. A method as claimed in claim 2, wherein the bleaching chemical is peroxide.

4. A method as claimed in claim 1, wherein the second sample volume pushed out from the first sample is collected in a level vessel communicating with a measurement container containing the first sample.

5. A method as claimed in claim 1, wherein the bleaching substance to be measured is peroxide.

\* \* \* \* \*